United States Patent
Wind

(10) Patent No.: US 10,806,813 B1
(45) Date of Patent: Oct. 20, 2020

(54) MARKING DEVICE

(71) Applicant: Brian E. Wind, North Canton, OH (US)

(72) Inventor: Brian E. Wind, North Canton, OH (US)

( * ) Notice: Subject to any disclaimer, the term of this patent is extended or adjusted under 35 U.S.C. 154(b) by 6 days.

(21) Appl. No.: 16/457,969

(22) Filed: Jun. 29, 2019

(51) Int. Cl.
*A61L 2/10* (2006.01)
*B43K 23/12* (2006.01)
*A61B 90/00* (2016.01)

(52) U.S. Cl.
CPC .............. *A61L 2/10* (2013.01); *B43K 23/12* (2013.01); *A61B 2090/397* (2016.02); *A61B 2090/3937* (2016.02); *A61L 2202/14* (2013.01)

(58) Field of Classification Search
CPC .......... A61L 2/10; B43K 23/08; B43K 23/10; B43K 23/12; B43K 23/122; B43K 23/124; B43K 23/126; B43K 23/128; B43K 29/10
See application file for complete search history.

(56) References Cited

U.S. PATENT DOCUMENTS

| | | | | |
|---|---|---|---|---|
| 4,016,414 A | * | 4/1977 | Browning | B43K 29/10 362/118 |
| 4,509,875 A | * | 4/1985 | Shintani | B43K 8/024 401/17 |
| 5,711,626 A | * | 1/1998 | Kobayashi | B43K 1/086 401/219 |
| 6,039,928 A | * | 3/2000 | Roberts | A61L 2/10 422/186.3 |
| 6,565,802 B1 | * | 5/2003 | Hanley | A61L 2/10 422/22 |
| 7,070,352 B2 | * | 7/2006 | Iida | B43K 5/12 401/41 |
| 7,160,045 B2 | * | 1/2007 | Oas | B43K 8/03 362/118 |
| 7,642,524 B1 | * | 1/2010 | Alvarez | A61L 2/10 250/455.11 |
| 8,058,629 B2 | * | 11/2011 | Long | A61L 2/10 250/455.11 |
| 8,337,770 B2 | * | 12/2012 | Wind | A61L 2/10 422/186.3 |
| 9,162,001 B2 | * | 10/2015 | Sunkara | A61L 2/10 |
| 9,345,799 B1 | * | 5/2016 | Wind | B43K 23/02 |
| 9,409,438 B2 | * | 8/2016 | Ohtsuka | B43K 25/022 |
| 9,566,819 B2 | * | 2/2017 | McDowell | B43K 31/00 |
| 9,801,965 B2 | * | 10/2017 | Bettles | A61L 2/10 |
| 10,270,484 B2 | * | 4/2019 | Lambert | A61L 2/26 |
| 2010/0061887 A1 | * | 3/2010 | Harper | A61L 2/10 422/24 |
| 2014/0245866 A1 | * | 9/2014 | Hadlock | A61L 2/10 81/9.2 |
| 2017/0333618 A1 | * | 11/2017 | Krohn | A61M 5/001 |

* cited by examiner

*Primary Examiner* — David P Angwin
*Assistant Examiner* — Bradley S Oliver
(74) *Attorney, Agent, or Firm* — Robert R. Lech; Lech Law, LLC

(57) ABSTRACT

A marking device and a sanitization system are disclosed. The marking device comprises a marker and a cap constructed from material that allows UV-C light rays to pass through. In an alternate embodiment, the marking device may be double-sided. In some embodiments, the marking device may be used in conjunction with a sanitization device, and/or the marking device may comprise a tracking device such as an RFID tracking device.

17 Claims, 2 Drawing Sheets

MARKING DEVICE

TECHNICAL FIELD

The present application relates generally to writing instruments and other marking devices, and more particularly to a skin marking device configured to receive ultra violet (UV-C) light for sanitizing the device.

STATEMENT REGARDING FEDERALLY SPONSORED RESEARCH

No government monies were used in the development of the subject matter of this application.

BACKGROUND

UV-C radiation is a form of electromagnetic radiation that contains measurable wavelengths in the 4-400 nanometer range. UV-C radiation is a well-known sanitization agent. The ultraviolet light is effective at eradicating bacteria, viruses and other pathogens. The exposure to UV-C light necessary to kill bacteria (or the "kill" factor) is a product of time and intensity. Suitable wavelengths for sanitizing a writing instrument are in the range of 100-300 nanometers. The ideal UV-C germicidal wavelength is approximately 254-270 nanometers.

However, it is also understood that exposure to UV-C light at an intensity necessary for effective and efficient eradication or sanitization of pathogenic agents is harmful to the human body so appropriate protective shielding is utilized within the dispenser to prevent direct or reflected UV-C light from striking the human body. The UV-C radiation required to effectively eradicate most pathogenic agents will be an intensity ranging from 1000-100,000 microwatts/cm2 with an ideal range of 3,000-10,000 microwatts/cm2. One object of this invention is to provide a marking device with effectively eradicated pathogens or micro-organisms by exposing all surfaces of the marking device to direct (or reflected) exposure or contact with the UV-C radiation for a sufficient period of time. Ideally, the UV-C radiation exposure time period when using a UV-C light with a wavelength of approximately 254-270 nanometers at an intensity of 10,000 microwatts/cm2 is in the range of 80-110 seconds.

Various types of illumination lamps may be employed, such as for example, an UV-C light, a pulsed or flashed UV-C light, a germicidal UV-C flash light or LED (light emitting diodes), pulsed UV-C and/or any other disinfecting illumination source now known or later discovered in accordance with this invention. Ideally, the described marking devices will be used in conjunction with one or more UV-C lamps or LEDs which produce UV-C light wavelengths of approximately 254-270 nanometers.

Hand-held writing instruments are commonly utilized by medical personnel at hospitals and out-patient clinics that offer surgical services. Example uses of writing instruments by medical personnel include, for example, marking a patient's skin in preparation for a medical procedure, and making notations on a patient's medical chart or other paperwork. Infectious microorganisms including viruses and bacteria colonize on these writing instruments and promote the spread of communicable diseases from the common cold to more serious infections. The use of ultraviolet light for its purification and germicidal effects is well known. When administered at the desired wave lengths, durations, and intensities, ultraviolet light is able to kill a wide spectrum of microorganisms.

In some instances, medical personnel utilize ballpoint pens, such as for updating patient charts, and in other cases, medical personnel require marker style pens, such as for identifying surgical locations on a patient. More recently, medical personnel have been utilizing styli to update computerized patient records. Marker style pens typically require caps to prevent the marker tip from drying out. Accordingly, marker style pens have not been effective candidates for sterilization via an ultra violet pen sanitization device because the pen cap prevents ultra violet light from reaching the pen tip to properly sanitize it.

Accordingly, there is a need for an improved marker style pen that can be sanitized using an ultra violet sanitization device.

SUMMARY

According to a first aspect of the present application, an example marking device is disclosed. The example marking device comprises: a barrel, a writing tip, and a cap. The barrel has an axis and a first axial end, and the barrel defines a grip portion and a finial disposed at the axial end. The writing tip is disposed in proximity to the finial, and the cap is disposed in proximity to the writing tip. The cap is configured to cooperate with the barrel to form an air-resistant chamber around the writing tip. The cap is constructed from material that allows UV-C light rays to pass through.

According to a second aspect of the present application, an example sanitation system is disclosed. The example sanitation system comprises a marking device and a sanitization device configured to apply UV-C radiation to the marking device. The marking device comprises: a barrel, a writing tip, and a cap. The barrel has an axis and an axial end, and the barrel defines a grip portion and a finial disposed at the axial end. The writing tip is disposed in proximity to the finial, and the cap is disposed in proximity to the writing tip. The cap is configured to cooperate with the barrel to form an air-resistant chamber around the writing tip. The cap is constructed from material that allows UV-C light rays to pass through.

According to a first aspect of the present application, an example marking device is disclosed. The example marking device comprises: a barrel, a writing tip, and a cap. The barrel is comprised of a color-changing material that changes color upon exposure to UV-C light. The barrel has an axis and a first axial end, and the barrel defines a grip portion and a finial disposed at the axial end. The writing tip is disposed in proximity to the finial, and the cap is disposed in proximity to the writing tip. The cap is configured to cooperate with the barrel to form an air-resistant chamber around the writing tip. The cap is constructed from material that allows UV-C light rays to pass through

BRIEF DESCRIPTION OF THE DRAWINGS

The accompanying figures, which are incorporated in and constitute a part of the specification, illustrate various example systems and devices, and they are used merely to illustrate various example embodiments. Like reference numerals refer to identical or similar components or steps. It should be noted that the various components depicted in the figures may not be drawn to scale, and that the various assemblies and designs depicted in the figures are presented for purposes of illustration only, and should not be considered in any way as limiting.

DETAILED DESCRIPTION

Figure 1:
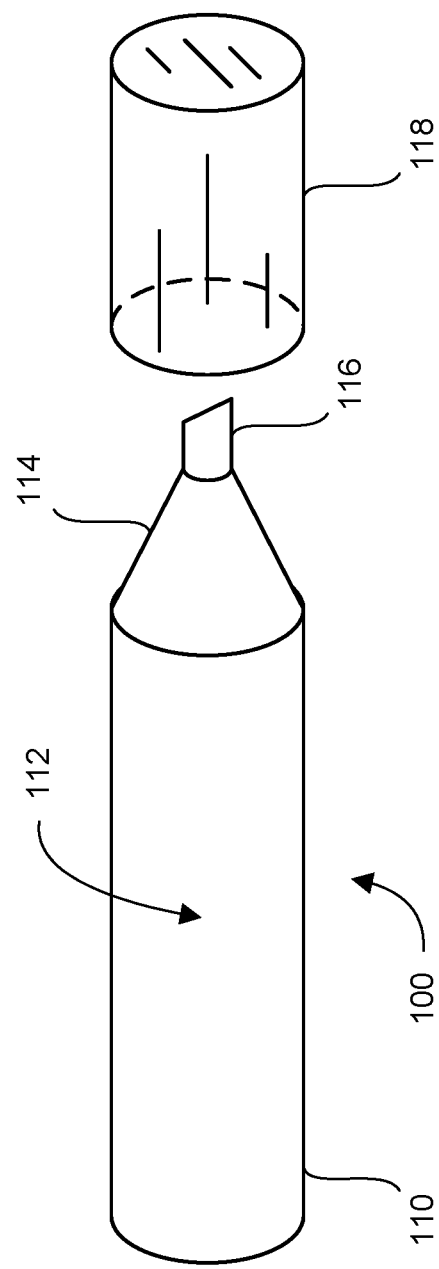
FIG. 1 illustrates a perspective view of a first example skin marking device having a single marking tip in accordance with the present application.

Particular embodiments of the present device will now be described in greater detail with reference to the figures. Like reference numerals apply to similar parts throughout the several views.

FIG. 1 illustrates an example skin marking device 100 which may be sanitized for use in medical applications. Marking device 100 comprises an axial barrel 110. Barrel 110 comprises a grip portion 112 which permits a user to grip marking device 100 during use. Barrel 110 further comprises a tapered portion, or finial, 114 disposed at a first axial end of barrel 110. Finial 114 cooperates with and supports a writing tip 116 which may apply marking fluid to a patient's skin.

Writing tip 116 may be constructed from felt or other porous material to promote the retention and application of marking fluid. In order to prevent the writing tip and/or the marking fluid from hardening and/or drying out, marking device 100 comprises a removable cap 118. Cap 118 may be removably secured to marking device 100 and may cooperate with the barrel 110, such by snapping the cap 118 onto barrel 110 in a conventional fashion, so as to define an air resistant chamber which protects the writing tip 116 from damage and/or drying out. Cap 118 is constructed from a UV-C transparent material. The UV-C transparent material of cap 118 enables the finial 114 and writing tip 116 to be sanitized upon exposure to UV-C radiation.

Figure 2:
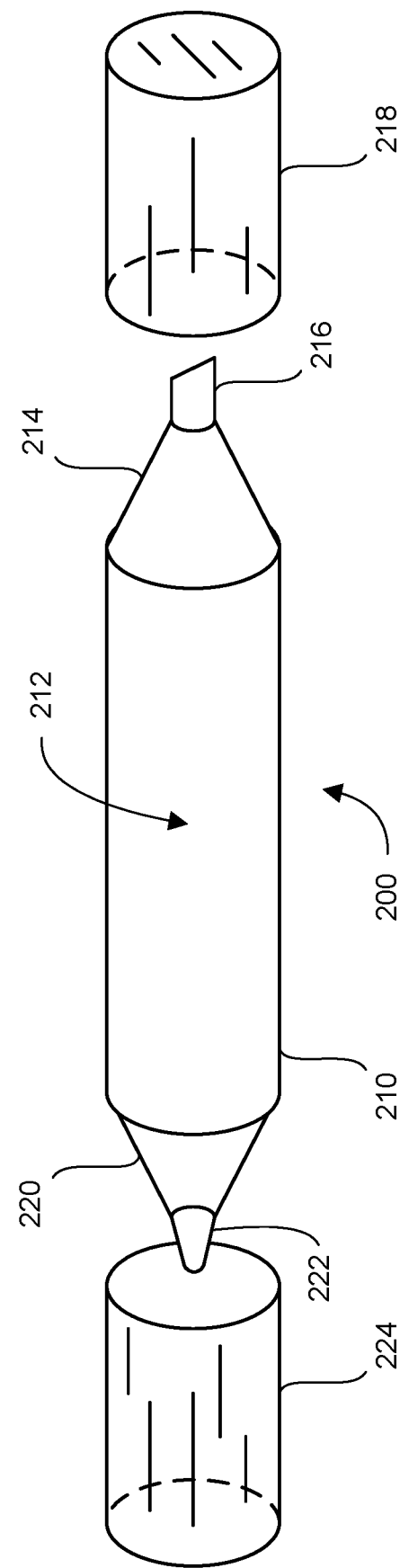
FIG. 2 illustrates a perspective view of a third example skin marking device having two marking tips in accordance with the present application.

Referring now to FIG. 2, a second example marking device 200 is illustrated. Marking device 200 is a double-sided marking device in that it has two writing tips, one at each axial end of marking device 200. Depending on the needs of the user, the two writing tips may be the same type of writing tip or two different types of writing tips.

Second example marking device 200 may comprise some of the same elements as marking device 100, including a barrel 210, a grip portion 212, a first finial 214, a first writing tip 216, and a first cap 218. In accordance with the double-sided nature of example marking device 200, it further comprises a second writing end comprising a second finial 220, a second writing tip 222, and a second cap 224.

The double-sided nature of example marking device 200 makes it particularly useful in environments in which medical personnel would conventionally require multiple marking devices for various different tasks. For example, in environments in which medical personnel have a need to mark a patient's body for surgery and a need to update paper records, it would be desirable to have a double-sided marking device having a marker and ballpoint pen writing tip. By combining two writing functions into a single device, example marking device 200 provides efficiency in that fewer marking devices need to be sanitized and fewer marking devices are likely to be misplaced.

Various embodiments of example marking device 200 are envisioned depending on the needs of the user. For example, in the illustrated embodiment first writing tip 216 is a marker, and second writing tip 222 is a ballpoint pen. Of course other combinations are possible, such as an embodiment in which first writing tip 216 is a marker, and second writing tip 222 is a stylus for updating computerized patient records using an electronic tablet or other similar device. Of course, those having ordinary skill in the art will recognize various other useful combinations, all of which are considered to be within the scope of the present application.

In embodiments in which second writing tip 222 is unlikely to dry out, such as for example, where second writing tip 222 is a ballpoint pen tip, second cap 224 may be optional.

Figure 3:
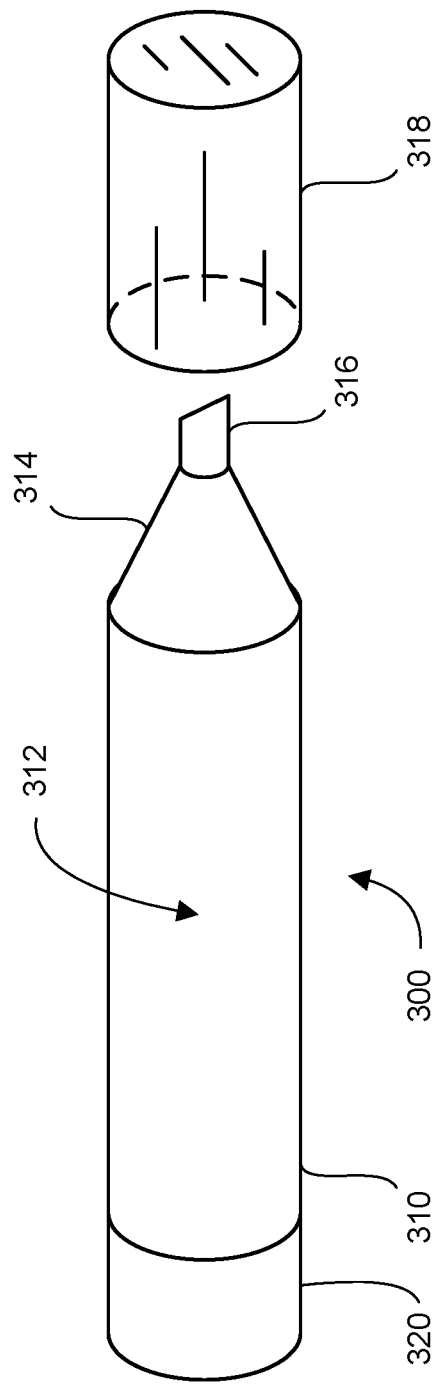
FIG. 3 illustrates a perspective view of a second example skin marking device having a tracking device in accordance with the present application.

Referring now to FIG. 3, a third example marking device 300 is illustrated. Third example marking device 300 may comprise many of the same elements as marking device 100, including a barrel 310, a grip portion 312, a finial 314, a writing tip 316, and a cap 318. In addition, third example marking device 300 comprises a tracking device 320, such as for example, an RFID tracking device.

The inclusion of tracking device 320 with third example marking device 300 enables a medical facility to control its inventory of marking devices. In conjunction with computerized inventory control and tracking applications, medical facilities may collect usage information that can assist in determining the most efficient number and locations for sanitation devices to be distributed within the facility.

Figure 4:
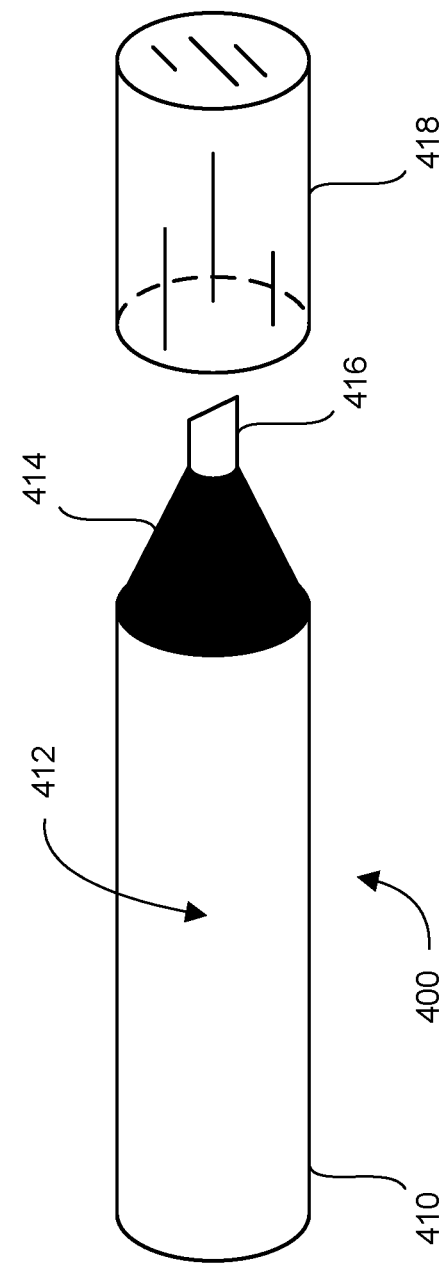
FIG. 4 illustrates a perspective view of a fourth example skin marking device comprising color-changing material in accordance with the present application.

Referring now to FIG. 4, a fourth example marking device 400 is illustrated. Fourth example marking device 400 may comprise many of the same elements as marking device 100, including a barrel 410, a grip portion 412, a finial 414, a writing tip 416, and a cap 418. Fourth example marking device 400 further comprises a color-changing material that changes color upon exposure to UV-C light. In the illustrated embodiment, finial 414 comprises such color-changing material. Finial 414 is illustrated as it might appear immediately after device 400 had been irradiated using UV-C light. Although in the illustrated embodiment, only finial 414 comprises the color-changing material, the present application is intended to cover embodiments in which all or any portion of barrel 410 comprises the color-changing material.

The color-changing material may act as an indicator of sanitation. When device 400 has not been sanitized, finial 414 will present a first color. After device 400 has been exposed to UV-C light, finial 414 will change to a different color. By observing the color of finial 414, a user is able to discern whether device 400 has been sanitized and may be safely used in certain medical environments. Because the color-changing material naturally returns to its base color over time, a user can further observe whether a particular sanitization is stale, or is unreliable.

One of ordinary skill in the art will appreciate that any of the marking devices described herein may form part of a more comprehensive sanitization system. For example, the marking devices described herein may cooperate with prior art sanitation devices configured to apply UV-C radiation to a marking device. Examples of such sanitation systems are described in U.S. Pat. Nos. 8,337,770 and 9,345,799, the entirety of which are hereby incorporated by reference.

While the systems, methods, and so on have been illustrated by describing examples, and while the examples have been described in considerable detail, it is not the intention of the applicant to restrict, or in any way, limit the scope of the appended claims to such detail. It is, of course, not possible to describe every conceivable combination of components or methodologies for purposes of describing the systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2*d*. Ed. 1995).

What is claimed is:

1. A marking device, comprising:
   a barrel, the barrel having: an axis, a first axial end, and a second axial end, the barrel defining: a grip portion and a first finial disposed at the first axial end;
   a first writing tip disposed in proximity to the first finial; and
   a first cap disposed in proximity to the first writing tip, the first cap configured to cooperate with the barrel to form an air-resistant chamber around the first writing tip, the first cap constructed from material that allows UV-C light rays to pass through.

2. The marking device of claim 1, wherein the barrel further defines a second finial disposed at the second axial end, and the marking device further comprises a second writing tip disposed in proximity to the second finial.

3. The marking device of claim 2 further comprising a second cap disposed in proximity to the second writing tip, the second cap configured to cooperate with the barrel to form an air-resistant chamber around the second writing tip, the second cap constructed from material that allows UV-C light rays to pass through.

4. The marking device of claim 2 wherein the first writing tip is a marker writing tip, and the second writing tip is a ball-point writing tip.

5. The marking device of claim 2 wherein the first writing tip is a marker writing tip, and the second writing tip is a stylus.

6. The marking device of claim 1 further comprising a tracking device.

7. The marking device of claim 6 wherein the tracking device comprises an RFID tracking device.

8. The marking device of claim 1 wherein the barrel comprises a color-changing material that changes color upon exposure to UV-C light.

9. A sanitization system comprising:
   a marking device comprising:
      a barrel, the barrel having: an axis, a first axial end, and a second axial end, the barrel defining: a grip portion and a first finial disposed at the first axial end;
      a first writing tip disposed in proximity to the first finial;
      a first cap disposed in proximity to the first writing tip, the first cap configured to cooperate with the barrel to form an air-resistant chamber around the first writing tip, the first cap constructed from material that allows UV-C-C light rays to pass through; and
   a sanitization device configured to apply UV-C radiation to the marking device.

10. The sanitization system of claim 9, wherein the barrel further defines a second finial disposed at the second axial end, and the marking device further comprises a second writing tip disposed in proximity to the second finial.

11. The sanitization system of claim 10, wherein the marking device further comprises a second cap disposed in proximity to the second writing tip, the second cap configured to cooperate with the barrel to form an air-resistant chamber around the second writing tip, the second cap constructed from material that allows UV-C light rays to pass through.

12. The sanitization system of claim 10 wherein the first writing tip is a marker writing tip, and the second writing tip is a ball-point writing tip.

13. The sanitization system of claim 10 wherein the first writing tip is a marker writing tip, and the second writing tip is a stylus.

14. The sanitization system of claim 9 further comprising a tracking device.

15. The sanitization system of claim 14 wherein the tracking device comprises an RFID tracking device.

16. The system of claim 9 wherein the barrel comprises a color-changing material that changes color upon exposure to UV-C light.

17. A marking device, comprising:
   a barrel, the barrel comprising a color-changing material that changes color upon exposure to UV-C light, the barrel having: an axis, a first axial end, and a second axial end, the barrel defining: a grip portion, a first finial disposed at the first axial end, and a second finial disposed at the second axial end;
   a first writing tip disposed in proximity to the first finial;
   a second writing tip disposed in proximity to the second finial; and
   a first cap disposed in proximity to the first writing tip, the first cap configured to cooperate with the barrel to form an air-resistant chamber around the first writing tip, the first cap constructed from material that allows UV-C light rays to pass through.

\* \* \* \* \*